United States Patent [19]
Bombardelli

[11] Patent Number: 5,955,489
[45] Date of Patent: Sep. 21, 1999

[54] TAXANE DERIVATIVES, THE PREPARATION THEREOF AND FORMULATIONS CONTAINING THEM

[75] Inventor: Ezio Bombardelli, Milan, Italy

[73] Assignee: Indea S.p.A., Milan, Italy

[21] Appl. No.: 09/155,959

[22] PCT Filed: Apr. 29, 1997

[86] PCT No.: PCT/EP97/02198

§ 371 Date: Oct. 6, 1998

§ 102(e) Date: Oct. 6, 1998

[87] PCT Pub. No.: WO97/43291

PCT Pub. Date: Nov. 20, 1997

[30] Foreign Application Priority Data

May 10, 1996 [IT] Italy .................................. MI96A0942

[51] Int. Cl.$^6$ ....................... A61K 31/415; C07D 491/06
[52] U.S. Cl. ...................................... 514/403; 548/358.1
[58] Field of Search ........................ 348/358.1; 514/403

[56] References Cited

FOREIGN PATENT DOCUMENTS

| | | |
|---|---|---|
| 0 253 738 | 1/1988 | European Pat. Off. . |
| MI95A1022 | 8/1997 | Italy . |
| MI95A0533 | 10/1997 | Italy . |
| WO 94 25441 | 11/1994 | WIPO . |

OTHER PUBLICATIONS

Journal of the American Chemical Society, vol. 93, No. 9, May 5, 1971, pp. 2325–2327, "Plant antitumor agents. VI The isolation and structure of taxol, a novel antileukemic and antitumor agent from Taxus brevifolia".

*Primary Examiner*—Robert W. Ramsuer
*Attorney, Agent, or Firm*—Pennie & Edmonds LLP

[57] ABSTRACT

The present invention relates to the preparation of taxane derivatives starting from 10-deacetyl-baccatine III, 14-hydroxy-10-deacetyl-baccatine 111, 19-hydroxy-10-deacetyl-baccatine III and their esters at $C_{13}$, reacting the respective 10-dehydro derivatives with hydrazine, hydroxylamine and derivatives thereof. The novel compounds contain a pyrazoline group involving the $C_7$ and $C_9$ carbons. The $C_{13}$ esters of these molecules with substituted isoserine chains exert antitumor activity inhibiting cell proliferation of normal and resistant tumor cell lines and inducing apoptosis. These molecules due to their basic character can be administered upon salification in an aqueous medium without requiring the use of toxic surfactants.

10 Claims, No Drawings

TAXANE DERIVATIVES, THE PREPARATION THEREOF AND FORMULATIONS CONTAINING THEM

This application is a 371 of PCT/EP97/02198 filed Apr. 29, 1997.

TECHNICAL FIELD

The present invention relates to taxane derivatives prepared starting from 10-deacetyl-baccatine III, 14-hydroxy-10-deacetyl-baccatine III, 19-hydroxy-10-deacetylbaccatine III and their esters at $C_{13}$, by reaction of the respective 10-dehydro-derivatives with hydrazine, hydroxylamine and derivatives thereof.

BACKGROUND ART

EP 253738 describes taxol derivatives bearing hydroxyls in positions 10 and 7 and a keto in position 9, which derivatives can be substituted by a isoserine residue in position 13; WO 94/25441 discloses anthrapyrazolones which can be used as anticancer agents, and a process for their synthesis; the "Journal of the American Chemical Society", vol. 93 No. 9, pages 2325–2327, reports the isolation and characterization of taxol derivatives having tumor inhibitory properties.

The novel compounds contain a pyrazoline group involving the $C_7$ and $C_9$ carbons. The esters at $C_{13}$ with isoserine chains functionalized at $C_3'$ and at NH have cytotoxic activity on the cell lines of the most common-human tumors as well as in vivo anti-cancer activity. The compounds of the invention are potent cytotoxic agents, particularly active on cells resistant to known antiblastics and are strong apoptosis inducers on these cell lines, which activity is significantly important in the oncologic therapy.

SUMMARY OF THE INVENTION

The derivatives of the present invention have the following general formula (1)

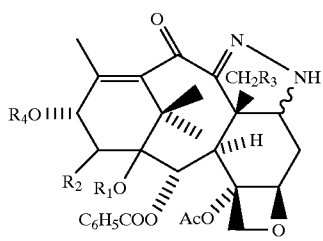

(1)

wherein $R_1$ and $R_2$ are hydrogen atoms or $R_1$ is hydrogen and $R_2$ is a hydroxy, alkoxy or acyloxy group, or $R_1$ and $R_2$ together form a cyclic carbonate or a cyclic thiocarbonate group of formula

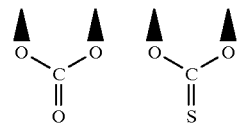

$R_3$ is hydrogen or hydroxy;
$R_4$ is hydrogen or an isoserine residue of formula (2)

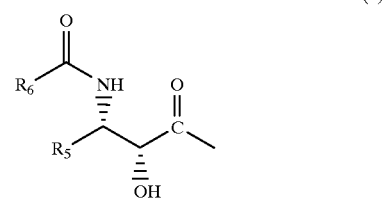

(2)

wherein $R_5$ is a $C_1$–$C_5$ alkyl or $C_2$–$C_5$ alkenyl group or an aryl residue, $R_6$ has the same meanings as $R_5$ or is a tert-butoxy group.

An aryl group is preferably a phenyl group. An alkoxy group is preferably a methoxy or ethoxy group. An acyloxy group is preferably an acetoxy group.

DETAILED DESCRIPTION OF THE INVENTION

The compounds of formula (1) are prepared starting from a taxane of formula (3)

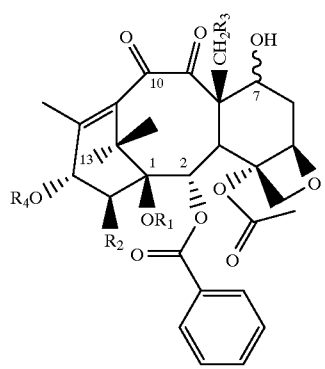

(3)

wherein $R_1$, $R_2$, $R_3$ and $R_4$ are as defined above, by reaction with hydrazine in alcohols, preferably in methanol.

The reaction yields two diastereomers in α and β at $C_7$ which can be separated by fractional crystallization or better by chromatography using for example silica gel columns and mixtures of ethyl acetate and hexane as eluents. In the reaction with hydrazine the isomer β forms preferably in an about 8:2 ratio. Therefore the two isomer forms are also an object of the present invention. The reaction can be applied, besides to baccatine III or 14-β-hydroxy-baccatine III or the corresponding carbonates or thiocarbonates prepared by reaction with phosgene or thiophosgene in pyridine (Italian patent appl. MI95A000533 and MI95O01022), also to the products already esterified at $C_{13}$, such as paclitaxel, cephalomannine, docetaxel and their semi-synthetic analogues. The above mentioned products, after removing the acetate at $C_{10}$ by treatment with hydrazine in methanol, are oxidized with copper acetate to 10-dehydro derivatives (see Italian patent applications cited above) which are directly converted into the corresponding pyrazoline derivatives by treatment with hydrazine. The conversion yields are nearly quantitative in the various steps. The pyrazoline derivatives can be used as such and have an activity comparable to or higher than the starting products as far as cytotoxicity is concerned. The obtained pyrazoline derivatives can be converted into the dihydro derivatives by catalytic hydrogenation or they can be derivatized at the nitrogen.

EXAMPLES

By way of example, the cytotoxicity of some of the prepared compounds is reported.

TABLE I $IC_{50}$ of compounds 2, 4, 5, 6, of paclitaxel and of docetaxel on a normal ovary cell line and on an adriamycin-resistant one

|  | $IC_{50}$ (nM) | |
| --- | --- | --- |
|  | Line MDA | Line MCF7-ADR$_r$ |
| Paclitaxel | 2.4 | 2600 |
| Docetaxel | 0.8 | 700 |
| Compound of example 2 | 3.1 | 600 |
| Compound of example 4 | 1.2 | 264 |
| Compound of example 5 | 1.4 | 190 |
| Compound of example 6 | 2.1 | 102 |

The compounds of the present invention comprise preferably compounds with the chain at $C_{13}$ modified compared with paclitaxel and docetaxel wherein the phenylisoserine phenyl has been substituted with an isobutyl, isobutenyl or propenyl group.

The compounds of the invention can be incorporated in conventional pharmaceutical formulations such as solutions of the active ingredient in polyoxyethylenated castor oil free in particular from metal cations affecting adversely both the stability of the active principles and their cardiotoxicity or in formulations containing other excipients such as polysorbates or phospholipids, forming liposomes with the latter. The compounds of the present invention can moreover be co-ground with cyclodextrin oligomers, in particular with β and γ cyclodextrin or salified with pharmaceutically acceptable acids to be subsequently administered in a completely aqueous medium. The following examples illustrate the invention.

Example 1

Synthesis of 10-deacetyl-10-dehydro-baccatine III 2- or β-pyrazoline

A suspension of 10-deacetyl-10-dehydro-baccatine III. (1 g, 1.845 mmol) in 15 ml of methanol was added with 11.7 ml of a 10% hydrazine solution (31.5 mmoles). The suspension was refluxed and after 10 min became clear. The reaction was controlled by TLC on silica gel observing the disappearance of 10-deacetyl-10-dehydro-baccatine III. ($CHCl_3$-Acetonitrile 2:1). After 2 h the reaction mixture was diluted with $H_2O$ made acidic with HCl (100 ml) and extracted with EtOAc. The organic phase was dried on $Na_2SO_4$ concentrated to dryness. The residue was purified by chromatography on a silica gel column (40 g of silica gel, eluent hexane-ethyl acetate 1:1). 687 mg of β pyrazoline and 208 mg of a pyrazoline were obtained, having the following physico-chemical and spectroscopical characteristics:

β pyrazoline: m.p. 195° C., MS$^+$ 538, $^1$H-NMR (CDCl$_3$) H2 5.80 d J 8.6, H3 3.16 d J 8.6, H5 5.04 dd J 9.5/4.5, H6a 2.43 ddd J 13.5/9.5/4.5, H6 2.20 dd J 13.5/13.5/4.5, H7 4.20 ddd J 15.5/4.5/3.0, H13 4.69, H14 2.34 m, H16 1.23 s, H17 1.15 s, H18 1.66 s, H19 1.50 s, H20a 4.47 d, J 8.6, H20b 4.33 d J 8.6, NH 6.44 br s, OH 2.33 brs/i,87 brs, Ac 2.26 s, Bz 8.14 brd 6.7.

α pyrazoline: m.p. 219–222° C., MS 538$^-$, $^1$H-NMR (CDCl$_3$) H2 6.04 d J 6.0, H3 3.71d J 6.0,H5 4.93 br d J 2.5, H6 2.06 td J14.0/14.0/2.5, 6' 1.85 m, H7 4.39 dd J14.0/4.2, H13 4.79, brdd J 10.0/6.5, 14a 2.46 dd J 15.0/10.0, 14b 1.88dd J15.0/6.5, H16 1.33s, H17 1.23 s, H18 1.74 brs, H19 1.70 s, $H_2O$ 4.38s, NH 6.34 brs, OH 2.63/2.00, Ac 2.36s, Bz 8.12 brd, /0.6.

Example 2

Synthesis of 10-deacetyl-10-dehydro-Paclitaxel pyrazoline 400 mg of 10-dehydro paclitaxel (0.49 mmol) were dissolved in 10 ml of methanol and added with 10 mol.eq. of a $NH_2NH_2$ (4.9 mmol, 1.5 ml) solution prepared diluting 1 ml of pure $NH_2NH_2$ in 10 ml of methanol. After 2 h the reaction mixture was diluted with water and 3 ml of dil. HCl and extracted with ethyl acetate. The organic phase was counter washed then dried over sodium sulfate and evaporated to dryness. The residue was chromatographed through 10 g of silica gel eluting with an hexane/ethyl acetate 1:1 mixture, recovering the fractions containing paclitaxel β pyrazoline. 250 mg of a compound having the following characteristics were obtained: m.p. 190° C., MS 823 (M$^+$ NH$_4$)$^+$ and $^1$H-NMR and $^{13}$C-NMR in agreement with the structure.

Example 3

Synthesis of 10-dehydro-13-(N-Boc-phenylisoserinyl)-10-deacetylbaccatine III 1 g of docetaxel was dissolved in 50 ml of dry methanol and added under stirring with 3.71 g of finely ground copper acetate; the reaction mixture was stirred for 6 h at room temperature. The undissolved copper acetate was filtered off and the solution was diluted with water and extracted with ethyl acetate. The organic phase was counter washed with an ammonia diluted solution, then dried and concentrated to dryness. A pale yellow solid was obtained in an 85% yield, corresponding to 10 dehydro-13-(N-Boc-phenylisoserinyl) 10-deacetyl-baccatine III. M$^+$ 801.

Example 4

Synthesis of 13-(N-Boc-phenylisoserinyl)-10-dehydro-10-deacetyl-baccatine III pyrazoline 390 mg of 10-dehydro-13-(N-Boc-phenylisoserinyl) 10deacetyl-baccatine III (0.49 mmol) were dissolved in 10 ml of methanol and added with 10 mol.eq. of a $NH_2NH_2$ (4.9 mmol, 1.5 ml) solution prepared diluting 1 ml of pure $NH_2NH_2$ in 10 ml of methanol. After 2 h the reaction mixture was diluted with water and 3 ml of dil. HCl and extracted with ethyl acetate. The organic phase was counter washed, dried over sodium sulfate and evaporated to dryness. The residue was chromatographed through 10 g of silica gel eluting with an hexane/ethyl acetate 1:1 mixture, recovering the fractions containing docetaxel β pyrazoline. 280 mg of a compound having the following characteristics were obtained: m.p. 190° C., MS 823 $(M^+ NH_4)^+$ and $^1$H-NMR and $^{13}$C-NMR in agreement with the structure.

Example 5

Synthesis of 13-(N-Boc-3'-isobutyl)-isoserinyl-10-dehydrobaccatine III pyrazoline A solution of 100 mg of 13-(N-Boc-3'-isobutyl)-isoserinyl-baccatine III (0.12 mmol) in 2 ml of ethanol was added with 10 mol.eq. of a 10% hydrazine ethanol solution, freshly prepared (1.2 mmol, 0.38 ml of the ethanol sol.), then 15 mol.eq. of hydrazine are added in two successive times, in a 12 h interval from each other. After three days the deacetylation reaction was completed and the mixture was diluted with water and 2 ml of dil. HCl and the whole was extracted with ethyl acetate. The organic phase was washed with water to neutrality, then dried and concentrated to dryness. The residue was chromatographed through a silica gel column eluting with an ethyl acetate/hexane 4:6 mixture. 67 mg of 13-(N-Boc-3'-isobutyl)-isoserinyl-10-deacetyl-baccatine III were obtained.

A solution of 57 mg of 13-(N-Boc-3'-isobutyl)-isoserinyl-10-deacetyl-baccatine III (0.07 mmol) in 3 ml of methanol was added with 15 mol.eq. of powdered Cu(OAc)$_2$ and the whole was stirred for 6 h. The reaction mixture was diluted with water and extracted with ethyl acetate; the organic phase was washed with ammonia, then with water to neutrality and concentrated to dryness. The residue was dissolved in 3 ml of methanol and added with 20 mol.eq. of a 10% hydrazine ethanol solution. The reaction mixture was refluxed for two hours, controlling the reaction by TLC until the reagents disappeared. The reaction mixture was diluted with water and dil. hydrochloric acid and then extracted with ethyl acetate. The organic phase was washed with water, dried and concentrated to dryness; the residue was chromatographed on silica gel eluting with hexane/ethyl acetate 1:1. 29.2 mg of β pyrazoline and 11 mg of α pyrazoline were obtained.

Example 6

Synthesis of 13-(N-Boc-phenyl-isoserinyl)-1,14-carbonate10-dehydro-10-deacetyl-baccatine III pyrazoline A solution of 100 mg of N-Boc 14-hydroxytaxol 1,14-carbonate (0.11 mmol) in 3 ml of MeOH was added with 10 mol.eq. of a freshly prepared 10% NH$_2$NH$_2$ ethanol solution (1.12 mmol, 0.36 ml of the ethanol sol.). After 12 hours, a further 10 mol.eq. (tot. mol.eq. added: 20) were added. The reaction was controlled by TLC (Ex-EtOAc 3:7). After 48 hours the reaction mixture was diluted with water and 2 ml of dil. HCl, extracted with EtOAc (×3), the organic phase was washed with brine, dried, filtered, evaporated and separated by CC (Ex-EtOAc 6:4 and then 5:5) to obtain 30 mg of the starting product and 40 mg of the 10-deacetyl derivative.

A solution of 40 mg of the 10-deacetyl derivative (0.05 mmol) in 3 ml of MeOH was added with 15 mol.eq. of powdered Cu(OAc)$_2$ (0.69 mmol, 138 mg). The reaction was controlled by TLC (Ex-EtOAc 3:7) which lasted 24 hours. The reaction was diluted with water and extracted with EtOAc (×3): the organic phase was washed with a NH$_3$:H$_2$O 1:5 solution (×2) and then with brine. The organic phase was evaporated to obtain a pale yellow solid in a nearly quantitative yield.

The crude product from the oxidation with Cu(OAc)$_2$ was dissolved in 2 ml of MeOH and added with 20 mol.eq. of a 10% NH$_2$NH$_2$ ethanol solution (0.8 mmol, 0.25 ml of ethanol sol.). The reaction mixture was refluxed for 2 hours, the reaction was controlled by TLC (Ex-EtOAc 3:7), then diluted with water, added with 2–3 ml of dil. HCl. and extracted with EtOAc (×3). The organic phase was washed with brine, dried, mixed, filtered, evaporated and separated by CC with Ex-EtOAc 6:4/5:5 to obtain 10.5 mg of pyrazoline (α and β mixture).

What is claimed is:

1. Compounds of formula (1):

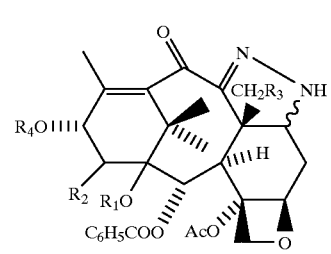

(1)

wherein R$_1$ and R$_2$ are hydrogen atoms or R$_1$ is hydrogen and R$_2$ is a hydroxy, alkoxy or acyloxy group, or R$_1$ and R$_2$ together form a cyclic carbonate or a cyclic thiocarbonate group of formula

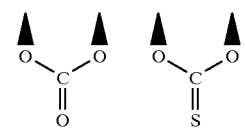

R$_3$ is hydrogen or hydroxy;
R$_4$ is hydrogen or an isoserine residue of formula (2)

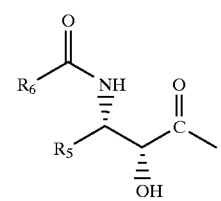

(2)

wherein R$_5$ is a C$_1$–C$_5$ alkyl or C$_2$–C$_5$ alkenyl group or a phenyl residue, R$_6$ has the same meanings as R$_5$ or is a tert-butoxy group.

2. A compound according to claim 1 wherein R$_1$, R$_2$, R$_3$ and R$_4$ are hydrogen.

3. A compound according to claim 1 wherein R$_1$, R$_2$, R$_3$ are hydrogen and R$_4$ is a residue of formula (2) wherein R$_5$ and R$_6$ are phenyl.

4. A compound according to claim 1 wherein $R_1$, $R_2$ and $R_3$ are hydrogen and $R_4$ is a residue of formula (2) wherein $R_5$ is phenyl and $R_6$ is tert-butoxy.

5. A compound according to claim 1 wherein $R_1$, $R_2$ and $R_3$ are hydrogen and $R_4$ is a residue of formula (2) wherein $R_5$ is isobutyl and $R_6$ is tert-butoxy.

6. A compound according to claim 1 wherein $R_1$ and $R_2$ form together a cyclic carbonate group, $R_3$ is hydrogen and $R_4$ is an isoserine residue wherein $R_5$ is phenyl and $R_6$ is tert-butoxy.

7. A compound according to claim 1 selected from the group consising of:
- 7-deoxy-9-deoxo-7-hydrazinyl-9-ylidene-10-deacetyl-10-dehydrobaccatin III (7α and 7β isomers);
- 7-deoxy-9-deoxo-7-hydrazinyl-9-ylidene-10-deacetyl-10-dehydropaclitaxel;
- 13-(N-BOC-phenylisoserinyl)-10-deacetyl-10-dehydrobaccatin III;
- 13-(N-BOC-phenylisoserinyl)-7-deoxy-9-deoxo-7-hydrazinyl-9-ylidene-10-deacetyl-10-dehydrobaccatin III;
- 13-(N-BOC-3'-isobutylisoserinyl)-7-deoxy-9-deoxo-7-hydrazinyl-9-ylidene-10-deacetyl-10-dehydrobaccatin III; and
- 13-(N-BOC-phenylisoserinyl)-7-deoxy-9-deoxo-7-hydrazinyl-9-ylidene-10-deacetyl-10-dehydro14β-hydroxybaccatin III-1,14-carbonate.

8. A process for the preparation of the compounds of claim 1 starting from a taxane of formula (3)

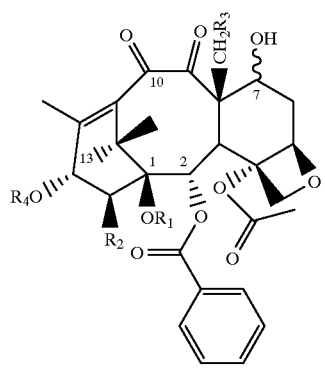

(3)

wherein $R_1$, $R_2$, $R_3$ and $R_4$ are as defined above, by reaction with hydrazine in alcohols.

9. A process according to claim 8 which is carried out in methanol.

10. Pharmaceutical compositions containing as the active ingredient a compound of claim 1 in admixture with a suitable carrier.

* * * * *

UNITED STATES PATENT AND TRADEMARK OFFICE
CERTIFICATE OF CORRECTION

PATENT NO.  : 5,955,489

DATED  : September 21, 1999

INVENTOR  : Ezio Bombardelli

It is certified that error appears in the above-identified patent and that said Letters Patent is hereby corrected as shown below:

On the title page at [73] Assignee: change "Indea S.p.A." to --Indena S.p.A.--.

Signed and Sealed this

Third Day of April, 2001

Attest:

NICHOLAS P. GODICI

*Attesting Officer*   Acting Director of the United States Patent and Trademark Office

UNITED STATES PATENT AND TRADEMARK OFFICE
CERTIFICATE OF CORRECTION

PATENT NO.   : 5,955,489
DATED        : September 21, 1999
INVENTOR(S)  : Ezio Bombardelli Page 1 of 1

It is certified that error appears in the above-identified patent and that said Letters Patent is hereby corrected as shown below:

Column 1,
Line 65, replace "$R_1$" with -- $OR_1$ --;

Column 6,
Line 36, please replace "$R_1$" with -- $OR_1$ --; and

Column 7,
Line 7, please replace "$R_1$" with -- $OR_1$ --.

Signed and Sealed this

Thirtieth Day of April, 2002

Attest:

Attesting Officer

JAMES E. ROGAN
*Director of the United States Patent and Trademark Office*